(12) United States Patent
Schiffrin et al.

(10) Patent No.: US 7,468,193 B2
(45) Date of Patent: Dec. 23, 2008

(54) NUTRITIONAL COMPOSITION AGAINST SIDE EFFECTS OF CHEMOTHERAPY OR RADIOTHERAPY

(75) Inventors: Eduardo Schiffrin, Crissier (CH); Denis Breuillé, Epalinges (CH); Stéphanie Blum-Sperisen, Mont-Pelerin (CH); Anne Donnet-Hughes, Saint-Legier (CH); Magali Faure, Mollie-Margot (CH); Claudia Roessle, Morges (CH); Marco Enrico Turini, Epalinges (CH)

(73) Assignee: Nestec S.A., Vevey (CH)

( * ) Notice: Subject to any disclaimer, the term of this patent is extended or adjusted under 35 U.S.C. 154(b) by 206 days.

(21) Appl. No.: 10/595,419

(22) PCT Filed: Oct. 14, 2004

(86) PCT No.: PCT/EP2004/011539

§ 371 (c)(1),
(2), (4) Date: Jul. 24, 2006

(87) PCT Pub. No.: WO2005/039318

PCT Pub. Date: May 6, 2005

(65) Prior Publication Data

US 2007/0042021 A1    Feb. 22, 2007

(30) Foreign Application Priority Data

Oct. 16, 2003  (EP) .................. 03023383

(51) Int. Cl.
*A61K 47/00*  (2006.01)
*A61K 38/00*  (2006.01)
*A01N 37/18*  (2006.01)

(52) U.S. Cl. .......................................... 424/439; 514/2
(58) Field of Classification Search ....................... None
See application file for complete search history.

(56) References Cited

U.S. PATENT DOCUMENTS

| 5,824,297 A | 10/1998 | Iwata et al. |
| 5,952,295 A | 9/1999 | Jaussan et al. |

FOREIGN PATENT DOCUMENTS

| EP | 0527283 | 2/1993 |
| EP | 0862863 | 9/1998 |
| EP | 0818529 | 2/2007 |
| WO | WO 96/34614 | 11/1996 |
| WO | WO 99/56758 | 11/1999 |
| WO | WO0144440 | 6/2001 |
| WO | WO 02/065840 | 8/2002 |
| WO | WO 02/083164 | 10/2002 |

OTHER PUBLICATIONS

Ayoub, I. et al., "Increase in the Proportion of CD4 T Lymphocytes and the Levels of Transforming Growth Factor-B in the Milk of Mastitic Cows," Immunology and Infectious Diseases, vol. 6, (1996), pp. 145-150.
Baites, W., "Lebensmittelchemie" pp. 330 (1995).
Land et al., "Transforming Growth Factor-B2 protects the small intestine during methotrexate treatment in rats possibly by reducing stem cell cycling," British Journal of Cancer, pp. 113-118 (2002).

*Primary Examiner*—Robert Landsman
(74) *Attorney, Agent, or Firm*—Gary M. Lobel

(57) ABSTRACT

The present invention relates to a nutritional composition suitable for patients undergoing chemotherapy and/or radiation such as cancer patients. The composition, which may be in powder or liquid form, comprises casein and whey proteins, TGF-β and free glutamine.

11 Claims, No Drawings

NUTRITIONAL COMPOSITION AGAINST SIDE EFFECTS OF CHEMOTHERAPY OR RADIOTHERAPY

BACKGROUND

The present invention relates to a nutritional composition suitable to treat or alleviate side-effects of treatment of cancer by chemotherapy or radiotherapy, both during and after such therapy. The invention also relates to a method for treating or preventing side effects of chemotherapy or radiotherapy.

Chemotherapy and radiotherapy are effective at destroying tumours because they target cells with high proliferation rates and hence fast growing tissues. Since stem cells of the gastrointestinal tract have high proliferation rates, too, a problematic side effect of chemotherapy or radiotherapy is the premature death of dividing epithelial cells.

In particular, chemotherapy and radiotherapy, which are often the treatments of choice for cancer patients, may be associated with symptoms of intestinal impairment such as nausea, vomiting, diarrhoea, with or without blood in the stools (ulceration) and abdominal pain. These symptoms are linked to damages of the intestinal mucosa, the epithelial cell layer lining the intestines, which is in direct contact with the contents of the gastro-intestinal tract. During chemotherapy, the gastro-intestinal tract often contains anti cancer drugs, which may induce dietary intolerance and mucositis. Stomatitis is also frequently observed, and, together with diarrhoea, this strongly hampers the quality of life of the patient.

Several products on the market are communicated to be beneficial for cancer patients. For example PROSURE™, which is commercialised by Abbott Laboratories is a ready-to-drink (rtd) beverage with an energy density of about 1.27 kcal/ml, about 21% of energy being provided by protein. Furthermore, the product has 0.021 g fibre per ml. However, a nutritional composition, which is even higher in energy and provides more protein may prove to be advantageous over this product.

RESOURCE SUPPORT™, a rtd drink commercialised by Novartis, has about 1.52 kcal/ml and 23.3% energy provided by protein. This formula has 0.127 g fibre per ml. It is an objective of the present invention to provide unique protein blends and a good taste adapted to cancer patients, while avoiding the presence of ingredients, which are present in amounts insufficient to be effective.

B van't Land et al, "Transforming Growth Factor-$\beta 2$ protects the small intestine during methotrexate treatment in rats possibly by reducing stem cell cycling", British Journal of Cancer (2002) 87, 113-118, report that TGF-$\beta 2$ isolated from bovine milk may reversibly arrest growth of epithelial stem cells during therapy. In a rat model, oral supplementation of rats exposed to methotrexate with TGF-$\beta 2$ reduced the chemotherapy-associated weight loss.

WO 96/34614 discloses a method for preventing the damage that chemotherapy causes to the lining of the alimentary tract, by administering an effective amount of a milk product extract. This extract comprises GFE-2 (Growth Factor Extract), which is isolated from whey and nearly free of casein.

U.S. Pat. No. 5,824,297 discloses the use of TGF-$\beta 3$ for inhibiting cytotoxic poisoning due to anti-neoplastic therapy such as radiation treatment or chemotherapy. TGF-$\beta 3$ is administered topically. U.S. Pat. No. 5,824,297 does not disclose a nutritional composition.

A food composition including colostrum-derived growth factors is disclosed in WO 99/56758, whereby the composition is administered to prevent a disorder of the gut, for example, resulting from chemotherapy. However, colostrum can be obtained only during a short period of time after birth of the calf. Furthermore, WO 99/56758 does not disclose an embodiment of a nutritionally complete composition.

In view of the prior art, it is an objective of the present invention to provide a nutritional composition, which is suitable to provide macro-nutrients and micro-nutrient and which prevents and/or alleviates mucosal damage, in particular those resulting from radiation or chemotherapy.

It is a particular objective to provide a good-tasting nutritional composition, which is suitable to promote weight gain in patients undergoing radiation- or chemotherapy. This objective is important in light of the fact that cancer patients that are chemically or radiation treated often have different taste preferences when compared to non-treated persons.

It is an objective of the present invention to provide nutrition and to prevent and/or treat side effects of chemotherapy or radiotherapy, for example with cancer patients.

Moreover, it is an objective to provide bio-active proteins derived or obtained from milk, which are able to remain active during passage through the gastro-intestinal tract.

It is an objective to provide a nutritional composition, comprising macro-nutrients, such as milk protein, which at the same time comprise bio-active proteins in effective quantities.

It is a further objective of the present invention to provide a nutritional supplement, for example a complete nutritional supplement.

SUMMARY

In a first aspect, the present invention provides a nutritional composition comprising a protein, a lipid and a carbohydrate source, which composition has an energy content of at least 1.3 kcal per ml, wherein the protein source provides from 20 to 30% of the energy of the composition, comprises from 40 to 80% by weight of casein and from 60 to 20% by weight of whey, comprises from 0.5 to 20 µg of TGF-$\beta$ per 100 kcal of the composition and comprises free glutamine in a quantity such as to provide from 2 to 15% of the energy of the composition.

In another aspect, the present invention the use of the composition in the manufacture of a nutritional formulation or supplement for alleviating and/or reducing side effects of chemotherapy and/or radiotherapy and to a method of providing nutrition to a cancer patient undergoing chemotherapy.

Additional features and advantages are described herein, and will be apparent from, the following Detailed Description.

DETAILED DESCRIPTION

Within the context of this specification the word "comprises" is taken to mean "includes, among other things". It is not intended to be construed as "consists of only".

The term "energy of the composition", as provided by a particular nutrient of the nutritional composition according to the present invention, is to be understood as "total energy of the composition", referring to the energy provided by all macro-nutrients together The term TGF-$\beta$ in an "active form" refers to TGF-$\beta$ that has maintained the full biological activity. Hence, this term also refers to TGF-$\beta$, which is not active but may be activated by external conditions, in particular by passage through the gastro-intestinal tract. This may be evaluated in models that simulate the acidity of stomach or duodenum.

In the context of the present invention, the term "protein source" includes any amino-acid-based proteinogenic matter, such as intact or hydrolysed dietetic protein, as well as added peptides or free amino acids and mixtures of these, for example.

In a preferred embodiment of composition according to the present invention, the protein source includes from 40 to 80% by weight of casein and from 60 to 20% by weight of whey.

Preferably, the protein source comprises 45-75%, more preferably 50-70% and most preferably 55-65% by weight of casein. Preferably, the protein source comprises 55-25%, more preferably 50-30%, more preferably 45-35% of whey protein.

The casein may be provided in free form or in the form of a salt, for example, a sodium salt. It is also possible to provide the casein as a calcium or potassium-salt.

TGF-β is a particularly important bio-active protein. Therefore, the composition of the present invention provides from 0.5 to 20 µg TGF-β, preferably TGF-β2. The TGF-β2 may be naturally present in an active form in the casein, for example if acid casein produced by mild processing is used. An example of such a process is where casein is precipitated by lowering the pH of milk with decationised whey and/or milk as described, for example, in FR 1 469 793 which discloses a process for obtaining casein by precipitating casein by lowering the pH with decationised whey. This process serves for the concurrent production of whey for the manufacture of lactose and nutritional compositions for mast. In this process the whey used as precipitation agent has preferably been liberated at least partially from lactose and/or albumin before the treatment of exchange of cations. For example, the whey may be obtained by diluting the slurry of whey after removal of lactose in view of raising its pH to 4.3 to 4.8, with the aid of a product like sweet whey of cheese or the water after rinsing the lactose, then heating (the diluted whey) to 90 to 95° C., and, after having eliminated the albumin in so doing, treating it in a cation-exchanger.

Surprisingly, by providing casein containing TGF-β2 obtained by a "mild" process as depicted above, the TGF-β2 is not inactivated during processing due to denaturation of protein. Furthermore, TGF-β2 could be in inactive form—complexed to TGF-β binding protein—but will be activated during passage through the acidic environment of the stomach. Remarkably, the casein fraction obtained associates with and protects TGF-β2 and prevents its inactivation until arrival in the small intestine. It is further very surprising that casein with TGFβ2 is obtained, since TGF-β2 is a soluble factor, which is usually found in the whey fraction.

Due to the protective properties of the casein containing TGF-β2, the amount of TGF-β to be administered in order to obtain the beneficial effects claimed herein, may be lower as compared to other ways of administering TGF-β, which lack a protective principle.

In a preferred embodiment, of the composition according to the invention, the casein containing TGF-β comprises 0.25-5, preferably 0.3-2.5, more preferably 1-2 µg of active TGF-β2 per g of casein.

In a preferred embodiment, the composition according to the invention preferably comprises 0.5-20, preferably 0.8-6.5, most preferably 1.5-4 µg of active TGF-β2 per 100 kcal of the nutritional composition.

The whey protein used in the composition of the invention may be commercially obtained. Suppliers of milk products such as whey and whey fractions include Arla Foods Ingredients, Morinaga Milk Industry Co., Ltd (Japan) and Tatua in New Zealand. Glanbia Nutritionals, for example, markets the product Salibra™700, a whey concentrate, which also contains TGF-β.

The quantitative presence of TGF-β in commercially available sources may be assessed by ELISA-tests. For example, a quantitative ELISA kit is commercially available for bovine TGF-β2, from R&D Systems (Catalogue number, DB250).

The protein source also comprises glutamine in the form of an added amino acid. "Added amino acid", in the context of the present invention, refers to an amino acid that is not protein-bound, but which is added separately from typical dietetic protein sources, such as milk, meat and vegetable proteins. The added amino acid may be present as a free amino acid and/or as a di- and/or tri-peptide comprising the amino acid. For example, the glutamine may be added in the form of a di-peptide such as L-alanyl glutamine. The choice of format in which the glutamine is added will, to some extent, be dictated by whether the composition is sold as a powdered composition intended to be reconstituted with water immediately prior to consumption or whether it is sold as a liquid composition. In the former case, the free amino acid can be, and preferably will be, utilised for reasons of cost. However, free glutamine is not stable in a liquid environment therefore if the composition is to be sold as a liquid, glutamine will have to be added as a dipeptide or other liquid-stable form. A further possibility if the composition is to be supplied as a liquid would be for an appropriate quantity of powdered glutamine to included in modular form for mixing with the liquid immediately prior to consumption.

Preferably, the protein source comprises 50-85% by weight of casein and whey and 15-50% of added glutamine, more preferably, the protein source of the composition comprises 60-75% by weight of casein and whey and 25-40% by weight of added glutamine.

In terms of energy provided by the protein source, the protein source of the composition according to the present invention provides 20-30%, preferably, 21-29%, more preferably 22-27% of the energy of the nutritional composition.

Preferably, the casein and whey provides 10-22%, more preferably 15-20% of the energy of the nutritional composition. Preferably, added glutamine provides 4-13%, more preferably 6-10% of the energy of the nutritional composition.

Clearly the casein and whey proteins will themselves include some glutamine and preferably, the sum of protein-bound and added glutamine provides 7-15%, more preferably 8-12% of the energy of the composition.

The protein source according to the invention may be in the form of intact protein or may be hydrolysed. Preferably, however, the protein source comprises intact whey and casein protein.

The nutritional composition according to the present invention comprises a lipid source. Sources of lipids for use in the nutritional composition may be selected from olive oil, sunflower oil, (low erucic) rapeseed oil, hazelnut oil, safflower oil, soy oil, corn oil, coconut oil, milk fat, black currant seed oil, fish oil, palm oil, peanut oil, as well as single cell oils and mixtures of these, for example.

The lipid source may comprise saturated fatty acids (SFA), monounsaturated fatty acids (MUFA), and/or polyunsaturated fatty acids (PUFA). SFA may partially be present as medium chain triglycerides (MCT), MCT referring to triglycerides comprising $C_6$-$C_{12}$ fatty acids.

In a preferred embodiment of the present invention, the lipid source comprises, in percent by weight of the lipid source, 30-70%, preferably 40-60%, more preferably 45-55% of MCT.

Preferably, the lipid source provides 25-45%, preferably 30-40%, more preferably, 32-38% of the energy of the composition.

Preferably, the lipid source of the composition comprises n-3 and/or n-6 PUFA.

Preferably, the composition according to the invention comprises a n-6/n-3 fatty acid ratio in the range of 2/1 to 8/1, preferably 2/1 to 7/1, more preferably the ratio is in the range of about 2/1 to 5/1.

Preferably, 5-15%, more preferably 8-12%, for example 10% of total fatty acids of the lipid source are present in the form of n-3 fatty acids. Preferably, the n-3 fatty acid is selected from α-linolenic acid (18:3n-3), eicosapentaenoic acid (EPA, 20:5n-3), docosapentaenoic acid (DPA, 22:5n-3), or docosahexaenoic acid (DHA, 22:6n-3) or mixtures of these.

Preferably, n-3 fatty acids are present in an amount, which corresponds to 1-6 g, preferably 2-4 g of n-3 fatty acids per daily intake of the nutritional composition.

Preferably, the composition according to the invention comprises EPA and DHA at a EPA/DHA ratio of 1/1.5 to 1/2.5, for example 1/2. Since molecular weights of EPA and DHA are almost identical, these ratios may be regarded as weight or as molecular ratios.

The composition according the present invention comprises at least one source of digestible carbohydrates. The digestible carbohydrate source may be any suitable carbohydrate or carbohydrate mixtures. For example, the carbohydrate source may be maltodextrin, native or modified starch from tapioca, corn, rice, other cereals, potato, for example, or high amylose starch, sucrose, glucose, fructose, and/or mixtures thereof. Preferably, the digestible carbohydrate source comprises maltodextrin, more preferably maltodextrin and sucrose.

Preferably, the composition according to the present invention is clinically free of lactose. The term "clinically free of lactose" refers, in the context of the present invention, to nutritional compositions that have a maximum of 0.2 g lactose per 100 kcal of the composition. Preferably, the composition has less than 0.2, more preferably less than 0.17 g lactose per 100 kcal of the composition.

The digestible carbohydrate source, may provide 25% to 55% of the energy of the composition; preferably 30% to about 50%, more preferably 35 to 45%, most preferably 37 to 43% of the energy. For example, the carbohydrate source may provide about 40% of the energy of the composition.

The enteral composition preferably includes a complete vitamin and mineral profile. For example, sufficient vitamins and minerals may be provided to supply about 100% to about 250% of the recommended daily allowance of the vitamins and minerals per 1500 calories of the nutritional composition.

Various flavours, sweeteners and other additives may be present.

The composition may further comprise at least one prebiotic. The term prebiotic refers to dietary fibre or other food components that may serve as a substrate for beneficial intestinal bacteria. Preferably, the composition comprises at least one type of soluble fibre, which can serve as a prebiotic.

The prebiotic may be an oligosaccharide or a mixture of different oligo- and/or polysaccharides. Oligosaccharides may be selected from oligosaccharides based on raffinose, galactose, fructose, lactosucrose, xylose, for example. EP 0 307 523 discloses the literature according to which the oligosaccharides may be obtained.

Preferably, the prebiotic is selected from inulin and/or fructooligosaccharides or a combination thereof.

Inulin is a mixture of fructose polymers ($F_2$—$F_{60}$), which may be isolated from chicory root by hot water extraction, for example. Inulin, which is obtained in this way is nearly always characterised by a final glucose unit, following the general formula GFn, where n lies between 2-60, preferably between 11-50. Inulin is commercially obtainable from "Orafti", Belgium, under the trade name Raftiline®, or from Cosucra, under the tradename Frutafit®.

Fructooligasaccharides (FOS) are generally oligopolymers of fructose, which may be obtained in at least two different ways:

(1) hydrolysis of inulin (see above), commercially obtainable from "Orafti", Belgium, under the various different trade names of Raftilose®.

(2) by synthesis from sucrose with the aid of β-fructofuranosidase from *Aspergillus niger*, commercially obtainable from Meiji Seika Co. of Japan. This latter method does not yield oligosaccharides of more than 5 fructose monosaccharide units (so-called short-chain, SC FOS).

The composition according to the invention preferably comprises a mixture of inulin and FOS, which comprises about 30-80% FOS and 20-70% inulin.

The composition may also comprise other prebiotics, such as further soluble non-starch polysaccharides. For the categorisation of fibre in soluble and insoluble fibre according to solubility in water, the standard protocol is found in L. Prosky et al., J. Assoc. Off. Anal. Chem. 71, 1017-1023 (1988). Examples of typically soluble non-starch polysaccharides are inulin, pectin, β-glucans, various gums such as gum Arabic, tragacanth, mucilages, guar and locust bean gum, agar, carageenans, alginates, xanthan and the like. These ingredients are commercially available.

A typical source of soluble fibre is pea inner fibre, also known as pea cellular wall, commercially obtainable from Cosucra under the trade name Sweelite®.

Preferably, the composition comprises, in percent by weight of dry matter, 0-10%, preferably 1-8%, more preferably, 2-5% of a prebiotic.

Preferably, the composition according to the invention comprises one or more probiotics, that is, micro organisms or their fermentation substrate that exert a beneficial effect on the consumer.

Probiotics may be either obtained commercially or they may be produced generally by a fermentation process and, optional, drying. Specific strains often have particular media or substrate preferences, which the skilled person knows about.

The micro-organisms may be in a dried form, or for example in a spore form for micro-organisms which form spores. The drying of micro-organisms after production by fermentation is known to the skilled person. See for example, EP 0 818 529 (SOCIETE DES PRODUITS NESTLE), where a drying process of pulverisation is described, or WO 0144440 (INRA). Usually, bacterial micro-organisms are concentrated from a medium and dried by spray drying, fluidised bed drying, lyophilisation (freeze drying) or another adequate drying process. For example, micro-organisms are mixed with a carrier material such as a carbohydrate, for example sucrose, lactose or maltodextrin, a lipid or a protein, for example milk powder during or before the drying.

However, the micro-organisms need not necessarily be present in a dried form. It may also be suitable to mix them directly after fermentation with a powdered nutritional composition, for example, and optionally perform a drying process, preferably at low temperatures (below 70° C.) thereafter. Such an approach is disclosed in WO 02065840 (SOCIETE DES PRODUITS NESTLE).

Many probiotics are commercially available and may be obtained in a powdered form various suppliers, for example, *Bifidobacterium lactis* (DSM 20215) may be obtained from Christian Hansen BioSystems A/S (CHL), 10-12 Boge Allé, P.O Box 407, DK-2970 Horsholm, Denmark. Such powders may be directly added (dry-mixed) to powdered nutritional compositions.

The literature mentions some of the micro-organisms from which suitable probiotics may be selected. For example, EP 0 862 863A2, in particular on page 3, lines 25-37, comprises a list from which the probiotic according to the present invention may be selected.

For example, the selected probiotic is a *Bifidobacterium*. Preferably, it is a *Bifidobacterium lactis* or a *Bifidobacterium longum*.

For example, the selected probiotic is a *Lactobacillus paracasei*. Preferably, the selected probiotic is selected from the group consisting of *Bifidobacterium longum* (CNCM I-2170), *Bifidobacterium lactis* (German Culture Collection: DSM20215), *Lactobacillus paracasei* (CNCM I-2116, CNCM I-1292), *Lactobacillus johnsonii* (CNCM I-1225) or mixtures thereof.

The term probiotic also includes dead probiotic bacteria, fermentation substrate and/or probiotic-derived material.

For example, the nutritional composition according to the invention may comprise $10^5$-$10^{11}$, more preferably $10^6$-$10^9$ cfu per daily serving of the nutritional composition. If the composition of the invention serves as complete nutrition, the daily serving may be divided up in several servings and corresponds to about 1.5 to 2 L of the nutritional composition of the invention, optionally if reconstituted.

If the composition is powdered, it preferably comprises $10^6$-$10^{11}$ cfu per 75 g of the powdered composition.

Preferably, the energy content of the composition according to the present invention is between 1.3-1.8 kcal/ml, more preferably 1.4-1.6 kcal/ml.

The composition may be used as a supplement to an individual's diet, however, it may also be designed to provide complete nutritional support.

As previously noted, the composition according to the invention may be sold in powder or liquid form. If in powder form, it may be reconstituted by the addition of water, such as boiled and cooled tap water, or otherwise nutritionally safe water. It will be appreciated that, in the case of a powdered composition, the stated energy content in kcal/ml refers, as is customary in this field, to the energy content of the composition after re-constitution with water in accordance with the instructions provided. For example, 50-100 g, more preferably 60-90 g of the powdered composition are mixed with 180 ml water and shaken or stirred.

The composition may be tube fed but is preferably administered orally which enables the composition to come into contact with the oral epithelial cells which are often severely affected by chemotherapy in particular.

The composition in powder form may also be reconstituted with juice, such as apple juice, flavoured waters or other beverages. Preferably, these beverages have a neutral pH. However, if the liquid used for reconstitution itself has a caloric content, it is advisable to reduce the amount of powder per 100 ml of liquid as compared with water in order that the made up composition does not have too high an energy content.

When the composition of the invention is used to provide complete nutrition, preferably, 1.0-2.5, more preferably 1.2-2.0 L, for example 1.5 L of the composition (reconstituted if necessary) are administered per day.

According to an embodiment of the invention, the composition is used for alleviating and/or reducing those side effects of chemotherapy and/or radiotherapy that are attributable to damage to the gastrointestinal tract. Such side effects may include ulceration, particularly in the mouth, diarrhoea, stomatitis, mucositis generally, infections, increased intestinal permeability, reduced absorption of nutrients and. In addition to side effects which have a direct and evident cause such as increased intestinal permeability (due to oxidative stress on the mucosal cells), patients suffering from cancer and undergoing chemotherapy or radiotherapy to treat the cancer often do not want to eat because eating is painful due to mouth ulcers for example or because they have altered perceptions of taste or feelings of nausea. These essentially psychological side effects are another reason why it is often difficult to maintain nutritional status in patients during periods of chemotherapy and radiotherapy.

The composition of the present invention may thus also be used in the preparation of nutritional formulations, medicaments or other forms of orally administered therapy for treating, preventing or alleviating side effects of radiotherapy and chemotherapy.

The nutritional composition according to the invention may be produced as is conventional; for example, by blending together the protein source, the carbohydrate source, and the lipid source. Emulsifiers may be included in the blend. Vitamins and minerals may be added at this point but may also be added later to avoid thermal degradation. Any lipophilic vitamins, emulsifiers and the like may be dissolved into the lipid source prior to blending. Water, preferably water, which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture is then homogenised. The homogenised mixture may then be further cooled to add any heat sensitive components; such as vitamins and minerals. The pH and solids content of the homogenised mixture is conveniently standardised at this point.

If the composition is to be sold as a powder, the mixture is then evaporated and dried to powder; for example by spray drying. Conventional procedures may be used. Probiotics and further heat sensitive ingredients, if not added before drying, such as certain minerals may now be added to the dried composition.

If the mixture is to be sold as a liquid, it will be adjusted to the appropriate concentration if necessary and subjected to conventional packaging processes such as retorting of filled containers or thermal processing followed by aseptic filling of the desired containers.

EXAMPLE 1

A powdered nutritional composition is prepared with the ingredients given in Table 1 below.

| Ingredient | g/100 g of dried components | Energy (1.5 kcal per ml) |
|---|---|---|
| Protein source (total): | 30 | 25% |
| Casein | 12.2 | 10.2% |
| Whey | 8.2 | 6.8% |
| Glutamine | 9.6 | 8% |

-continued

| Ingredient | g/100 g of dried components | Energy (1.5 kcal per ml) |
|---|---|---|
| Lipid source (total): | 18.4 | 35% |
| MCT (Coconut oil) | 9.2 | |
| Other lipids | 9.2 | |
| n-6/n-3 ratio | 2/1 | |
| Carbohydrates (total): | 47.4 | 40% |
| Maltodextrin | | |
| Vitamins and minerals are added according to daily requirements (total): | 60 mg | |

In order to prepare a powdered, reconstituted nutritional composition, the maltodextrin, neutralized acid casein, whey powder and amino acids are hydrated in tap water at about 50-60° C. to obtain a solution (the term solution is used to include the technical terms dispersion or suspension). The solution is standardised to a total solids content (TS) of 25%. Hydration time is adapted to have a good hydration of the protein.

Vitamins and minerals are added to the solution.

The pH is adjusted with KOH or citric acid to a value between 6.8-7.

The solution is pre-heated to 50° C. The lipid source, which comprises MCT, low erucic rapeseed oil, and corn oil, is pre-heated separately then added in-line and the mixture is heated to 105° C. by direct steam injection and this temperature is held for 5 seconds.

Then the product is directly flashed into an evaporator, in which the product is concentrated up to 40-50% total solids (dry matter) by a Scheffers falling-film evaporator.

Thereafter, the concentrated solution is held in a buffer tank for homogenisation, where it is pre-heated to 75° C., homogenised at 150 bars with a high pressure pump and then spray dried.

The powder is then mixed with Soya Lecithin and vitamin and mineral premixes, and a small part of the maltodextrin.

The powder may be filled into gassed cans or gassed pouches under an inert atmosphere of $N_2$ and $CO_2$.

The powder obtained is a nutritional composition particularly suitable as complete nutrition for patients undergoing anti-cancer treatments. The powder may be reconstituted with tap water. The recommended daily serving size for an adult patient would be 152 g powder per day.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A nutritional composition, wherein said nutritional composition has an energy content between 1.4-1.6 kcal per ml of said composition and comprises:
   a) a lipid source,
   b) a carbohydrate source,
   c) a protein source that provides from 20 to 30% of the energy of the composition and comprises casein, whey and TGF-β; and
   d) free glutamine in a quantity such as to provide from 2 to 15% of the energy of said composition; and
   wherein the remainder of said nutritional composition comprises 40 to 80% by weight of casein, from 60-20% by weight of whey; and from 0.5 to 20 μg of TGF-β3 per 100 kcal of the composition.

2. The composition according to claim 1, wherein said TGF-β is TGF β2 provided by acid casein and wherein said casein contains at least enough acid casein to provide the TGF-β2.

3. The composition according to claim 2, wherein TGF-β2 is from 1.5 to 4 μg per 100 kcal of the composition.

4. The composition according to claim 1, wherein the free glutamine provides from 5 to 10% of the energy of the composition.

5. The composition according to claim 1, wherein the lipid source provides from 25 to 45% of the energy of the composition.

6. The composition according to claim 1, wherein the lipid source comprises, in percent by weight of the lipid source, from 30 to 70% of medium chain triglycerides.

7. The composition according to claim 1, wherein the carbohydrate source provides from 25 to 55% of the energy of the composition.

8. A method for alleviating and/or reducing side effects of chemotherapy and/or radiotherapy in a patient comprising:
   administering to said patient an effective amount of a nutritional composition having an energy content between 1.4-1.6 kcal per ml of said composition, wherein said nutritional composition comprises:
   a) a lipid source;
   b) a carbohydrate source;
   c) a protein source that provides from 20 to 30% of the energy of the composition and comprises casein, whey and TGF-β; and
   d) free glutamine in a quantity such as to provide from 2 to 15% of the energy of said composition,
   wherein the remainder of said nutritional composition comprises 40 to 80% by weight of casein, from 60-20% by weight of whey; and from 0.5 to 20 μg of TGF-β per 100 kcal of the composition.

9. The method of claim 8, wherein said side effects of chemotherapy and/or radiotherapy are selected from the group consisting of diarrhoea, stomatitis, mucositis and increased intestinal permeability.

10. A method for providing nutrition to a patient suffering from cancer during periods of chemotherapy and/or radiotherapy treatment and immediately after such periods of treatment comprising:
    administering to said patient an effective amount of a nutritional composition having an energy content between 1.4-1.6 kcal per ml of said composition, wherein said nutritional composition comprises:
    a) a lipid source;
    b) a carbohydrate source;
    c) a protein source that provides from 20 to 30% of the energy of the composition and comprises casein, whey and TGF-β; and
    d) free glutamine in a quantity such as to provide from 2 to 15% of the energy of said composition,
    wherein the remainder of said nutritional composition comprises 40 to 80% by weight of casein, from 60-20% by weight of whey; and from 0.5 to 20 μg of TGF-β per 100 kcal of the composition.

11. A nutritional composition, wherein said nutritional composition has an energy content of 1.2 to 2 kcal per ml of said composition and comprises:

a lipid source,
a carbohydrate source,
a protein source that provides from 20 to 30% of the energy of the composition and comprises casein, whey and TGF-β; and
free glutamine in a quantity such as to provide from 2 to 15% of the energy of said composition; and
wherein the remainder of said nutritional composition comprises 40 to 80% by weight of casein, from 60-20% by weight of whey; and from 0.5 to 20 µg of TGF-β per 100 kcal of said composition.

* * * * *